United States Patent [19]

Woodruff et al.

[11] Patent Number: 5,102,868
[45] Date of Patent: Apr. 7, 1992

[54] METHOD FOR INHIBITING FOLLICULAR MATURATION

[75] Inventors: Teresa K. Woodruff; Jennie P. Mather, both of Millbrae, Calif.

[73] Assignee: Genentech, Inc., South San Francisco, Calif.

[21] Appl. No.: 461,705

[22] Filed: Jan. 8, 1990

[51] Int. Cl.$^5$ ................... A61K 37/24; A61K 37/02
[52] U.S. Cl. .......................................... 514/8; 514/12; 514/21; 424/559
[58] Field of Search ..................... 514/2, 12, 21, 8; 424/559

[56] References Cited

U.S. PATENT DOCUMENTS

| | | | |
|---|---|---|---|
| 4,734,398 | 3/1988 | di Zerega | 514/2 |
| 4,764,502 | 8/1988 | di Zerega | 514/2 |
| 4,798,885 | 1/1989 | Mason | 530/350 |
| 4,864,019 | 9/1989 | Vale et al. | 530/387 |
| 4,912,201 | 3/1990 | Di Zerega | 530/387 |

FOREIGN PATENT DOCUMENTS 0178841 4/1986 European Pat. Off. .

OTHER PUBLICATIONS

Tsafriri et al., Endocrin, 125:1857–1862 (1989).
Hsueh et al., PNAS U.S.A., 84:5082–5086 (1987).
de Kretser & Robertson, Biol. of Reprod., 40:33–47 (1989).
Ignotz & Massague, J. Biol. Chem., 261:4337–4345 (1986).
Adashi & Resnick, Endocrinology, 119:1879–1881 (1986).
Feng et al., J. Biol. Chem., 261:14167–14170 (1986).
Ying et al., BBRC, 136:969–975 (1986).
Hutchinson et al., BBRC, 146:1405–1412 (1987).
Mondschein et al., Endocrinology, 123:1970–1976 (1988).
Carson et al., J. Reprod. Fert., 85:735–746 (1989).
Gonzales-Manchon & Vale, Endocrinology, 125:1666–1672 (1989).
Baird et al., Ann. N.Y. Acad. Sci, 541:153–161 (1988).
De Jong, Physiol. Rev., 68(2):555–607 (1988).
Sheth & Moodbidri, Adv. Contracept., 2:131–139 (1986).
Findlay, Fertil. Steril., 46:770–783 (1986).
Baker et al., Clin. Reprod. & Fertil, 2:161–174 (1983).
Bremner et al., J. Clin. Invest., 68:1044–1052 (1981).
Lee & Gibson, Aust. J. Biol. Sci., 38:115–120 (1985).
McLachlan et al., Fertil. Steril., 48:1001–1005 (1987).
Cummins et al., J. Reprod. Fert., 77:365–372 (1986).
Henderson et al., J. Endocrin., 102:305–309 (1984).
Forage et al., J. Endocrin., 114:R1–R4 (1987).
Al-Obaidi et al., J. Reprod. Fert., 81:403–414 (1987).
Rivier & Vale, Endocrinology, 125:152–157 (1989).
Franchimont et al., Rev. for Gynecol. Obst., 83:607–611 (1988).
Woodruff et al., Science, 239:1296–1299 (1988).
Hasegawa et al., in "Inhibin: Non-Steroidal Regulation of FSH Secretion", ed. Burger et al., 42:119–133 (N.Y. Raven Press, 1987).
Woodruff et al., in "Growth Factors and the Ovary", Ed. Hirshfield, 291–295 (N.Y.: Plenum Press, 1989).
McLachlan et al., Lancet, 1:1233–1234 (1986).
Tsonis et al., J. Clin. Endocrin. Metab., 66:915–921 (1988).
Buckler et al., J. Endocrin, 122:279–285 (1989).
Tsuchiya et al., Fertil. Steril., 52:88–94 (1989).
Lefevre et al., Fertil., Steril., 46:325–327 (1986).
Tanabe et al., J. Clin. Endocrin. Metab., 57:24–31 (1983).
Yen & Jaffe, eds., Reproductive Endocrinology, Ed. 2, (Saunders, Philadelphia, 1986), p. 441.
Buckler et al., J. Clin. Endocrin. Metab., 66:798–803 (1988).
DiZerega, Nature 323:300 (1986).
Ono et al., Am. J. Obstet. Gynecol., 154(4):709–716 (1986).
Di Zerega et al., J. Steroid Biochem., 27375–383 (1987).
DiZerega et al., Meiotic Inhibiton: Molecular Control of Meiosis, pp. 201–226 (1988).
Tonetta & DiZerega, Endocr. Rev., 10:205–227 (1989).

*Primary Examiner*—F. T. Moezie
*Attorney, Agent, or Firm*—Janet E. Hasak

[57] ABSTRACT

A method is provided for inhibiting the maturation of follicles in the ovary of a femal mammal comprising administering to the ovary of the mammal an effective amount of activin. This method is particularly effective in treating polycystic ovarian disease.

7 Claims, 2 Drawing Sheets

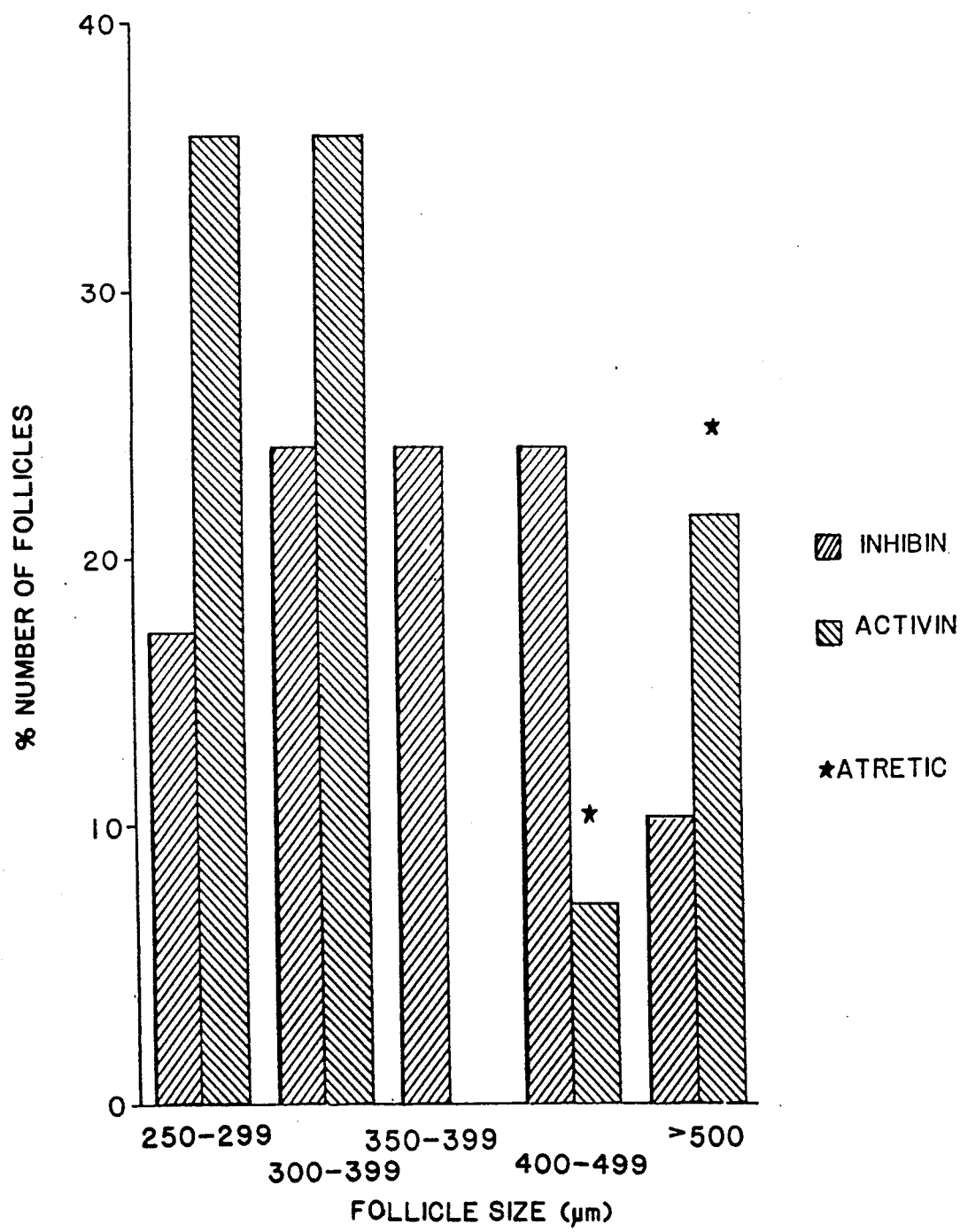

METHOD FOR INHIBITING FOLLICULAR MATURATION

FIELD OF THE INVENTION

This invention relates to a method for inhibiting follicular maturation in female mammals. In particular, this invention is directed to treating polycystic ovarian disease using activin.

DESCRIPTION OF RELATED ART

Inhibin is a glycoprotein produced by diverse tissues, including the gonads, pituitary, brain, bone marrow, placenta, and adrenal gland. It was initially identified by its ability to inhibit the secretion of follicle stimulating hormone (FSH) by the pituitary. De Jong and Sharpe, *Nature*, 263: 71-72 (1976); Schwartz and Channing, *Proc. Natl. Acad. Sci. USA*, 74: 5721-5724 (1977). Such preferential regulation of the gonadotropin secretion has generated a great deal of interest and prompted many laboratories in the past fifty years to attempt to isolate and characterize this substance from extracts of testis, spermatozoa, rete testis fluid, seminal plasma, and ovarian follicular fluid using various bioassays. Rivier et al., *Biochem. Biophys. Res. Commun.*, 133: 120 (1985); Ling et al., *Proc. Natl. Acad. Sci. USA*, 82: 7217 (1985); Fukuda et al., *Mol. Cell Endocrinol.*, 44: 55 (1985). The structure of inhibin, characterized from several species, consists of two disulfide-linked subunits: an $\alpha$ and either a $\beta A$ or a $\beta B$ chain.

After the identification of inhibin, activin was shown to exist in follicular fluid as a naturally occurring substance. Activin was found to be capable of stimulating FSH release by rat anterior pituitary cells. Vale et al., *Nature*, 321: 776-779 (1986); Ling et al., *Nature*, 321: 779-782 (1986). Activin consists of a homodimer or heterodimer of inhibin $\beta$ subunits, which may be $\beta A$ or $\beta B$ subunits. Vale et al., *Recent Prog. Horm. Res.*, 44: 1-34 (1988). There is 95-100% amino acid conservation of $\beta$ subunits among human, porcine, bovine, and rat activins. The $\beta A$ and $\beta B$ subunits within a given species are about 64-70% homologous. The activin $\beta A$ and $\beta B$ homodimers ("Activin A" and "Activin B," respectively) have been identified in follicular fluid, and both molecules have been cloned and their genes expressed. Mason et al., *Biochem. Biophys. Res. Commun.*, 135: 957 (1986); EP Pub. No. 222,491 published May 20, 1987; Mason et al., *Molecular Endocrinol.*, 3: 1352-1358 (1989). The complete sequence of the $\beta B$ subunit is published in Serono Symposium Publications, entitled "Inhibin-Non-Steroidal Regulation of Follicle Stimulating Hormone Secretion", eds. H. G. Burger et al., abstract by A. J. Mason et al., vol. 42, pp. 77-88 (Raven Press, 1987), entitled "Human Inhibin and Activin: Structure and Recombinant Expression in Mammalian Cells."

Both Activin A and Activin AB, but thus far not Activin B, have been isolated from natural sources. Activin mRNA ($\beta A$ and $\beta B$ subunits), bioactivity, and immunoactivity have been reported to be produced by testicular Leydig cells from immature rat and pig. Lee et al., *Science*, 243: 396-398 (1989); Lee et al., in Serono Symposium Publications, entitled "The Molecular and Cellular Endocrinology of the Testis" eds. Cooke and Sharpe, Vol. 50 (Raven Press: New York, 1988), p. 21-27. Activin A has been found recently to have erythropoietic-stimulating activity as well as FSH-releasing activity. See EP Publ. No. 210,461 published Feb. 4, 1987 (where the protein is called BUF-3), Eto et al., *Biochem. Biophys. Res. Commun.*, 142: 1095-1103 (1987) and Murata et al., *Proc. Natl. Acad. Sci. U.S.A.*, 85: 2434-2438 (1988) (where the activin is called EDF), and Yu et al., *Nature*, 330: 765-767 (1987) (where the activin is called FRP). In these systems, inhibin antagonized the actions of activin.

A protein known as follicle or follicular regulatory protein having a molecular weight of 12,000 to 15,000 is found to inhibit aromatase levels, modulate the formation of mature ova substantially independently of steroidal sex hormones, and reduce fertility in the male rat by systemic treatment. It does not directly affect the gonadotropin output of the pituitary. See U.S. Pat. No. 4,734,398; Tsutsumi et al., *Fertil. Steril.*, 47: 689 (1987); Lew et al., *Obstet. and Gynecol*, 70: 157-162 (1987); diZerega et al., *Meiotic Inhibition: Molecular Control of Meiosis* (Alan R. Liss, Inc., 1988), p. 201-226; diZerega et al., *J. Steroid Biochem.*, 27: 375-383 (1987); Montz et al., *Am. J. Obstet. Gynecol.*, 436-441 (Feb. 15, 1984); Ahmad et al., *the Anatomical Record*, 224: 508-513 (1989). This protein, also named FRP, has been purified and partially sequenced, and is not related in any way to the FSH-releasing protein known as activin, referred to as FRP by the Salk researchers in their early work.

Recently, the expression of inhibin subunits, each encoded by a separate gene, was demonstrated in several tissues in addition to ovary and testis. Inhibin $\alpha$, $\beta A$, and $\beta B$ mRNAs were detected in placental, pituitary, adrenal, bone marrow, kidney, spinal cord, and brain tissues. Meunier et al., *Proc. Natl. Acad. Sci. USA*, 85: 247 (1988). The expression of the inhibin subunit mRNAs varied by several-fold in a tissue-specific manner, suggesting different functions for these proteins depending on their pattern of association and their site of production.

Inhibin and activin are members of a family of growth and differentiation factors. The prototype of this family is transforming growth factor-beta (TGF-$\beta$) (Derynck et al., *Nature*, 316: 701-705 (1985)), Which, according to one source, possesses FSH-releasing activity. Ying et al., *Biochem. Biophys. Res. Commun.*, 135: 950-956 (1986). Other members of the TGF-$\beta$ family include the Mullerian inhibitory substance, the fly decapentaplegic gene complex, and the product of Xenopus Vg-1 mRNA.

In the human, growing preovulatory follicles and corpus luteum secrete inhibin into the circulation in response to FSH stimulation. Lee and Gibson, *Aust. J. Biol. Sci*, 38: 115-120 (1985); McLachlan et al., *Fertil. Steril.*, 48: 1001 (1987). Thus, inhibin-related peptides play important roles in the modulation of gonadal functions via a pituitary feedback loop. In rat primary cultures of testis cells and ovarian thecal-interstitial cells, inhibin has been reported to enhance androgen biosynthesis stimulated by leutinizing hormone (LH), whereas activin suppresses androgen production. Hsueh et al., *Proc. Natl. Acad. Sci. USA*, 84: 5082-5086 (1987). Other workers have been unable to repeat these observations. deKretser and Robertson, *Biology of Reproduction*, 40: 33-47 (1989). Inhibitory effects of TGF-$\beta$ on Leydig cell steroidogenesis have also been described. Lin et al., *Biochem. Biophys. Res. Commun.*, 146: 387 (1987); Fauser and Hsueh, *Life Sci.*, 43: 1363 (1988); Avallet et al., *Biochem. Biophys. Res. Commun.*, 146: 575 (1987). In granulosa cells, activin has been reported to inhibit (and TGF-$\beta$ to enhance) progesterone production. Ignotz and Massague, *J. Biol. Chem.*, 261: 4337 (1986). In primary cultures of granulosa cells, activin and inhibin as well as TGF-β were found to affect hormone synthesis and secretion, each in a different fashion. Adashi and Resnick, *Endocrinology*, 119: 1879 (1986); Ying et al., *Biochem. Biophys. Res. Commun.*, 136: 969 (1986); Hutchinson et al., *Biochem. Biophys. Res. Commun.*, 146: 1405 (1987); Mondschein et al., *Endocrinology*, 123: 1970 (1988); Feng et al., *J. Biol. Chem.*, 261: 14167 (1986). These molecules have both positive and negative effects on FSH-dependent granulosa cell function. Carson et al., *J. Reprod. Fert.*, 85: 735–746 (1989). Also suggested is that individual members of the TGF-β/inhibin gene family regulate ovarian function, not only by direct action on follicle cells, but also indirectly by influencing the production rate of other members of that family. Zhiwen et al., *Molecular and Cellular Endocrinology*, 58: 161–166 (1988).

Activin A and inhibin were reported to modulate growth of two gonadal cell lines, suggesting that these proteins may regulate proliferation as well as functions of gonadal cells. Gonzalez-Manchon and Vale, *Endocrinology*, 125: 1666–1672 (1989). The secretion of inhibin by the corpus luteum has been proposed to suppress the concentration of FSH in the luteal phase of the cycle and hence the inhibition of follicular development. Baird et al., *Ann. N.Y. Acad. Sci.*, 541: 153–161 (1988).

A review article postulates that inhibin is at least one of the factors that determines the number of follicles destined to ovulate, and that interference with the action of inhibin might contribute to the regulation of fertility. De Jong, *Physiol. Rev.* 68: 555 (1988). Many investigators have speculated that due to its FSH-inhibiting effect at the level of the pituitary, inhibin may be useful in male and female contraception. Sheth and Moodbidri, *Adv. Contracept.* 2: 131–139 (1986); Findlay, *Fertil. Steril.*, 46: 770 (1986). However, another author doubts that inhibin can inhibit spermatogenesis (citing Bremner et al., *J. Clin. Invest.*, 68: 1044 (1981)), and states that inhibin might also have some direct stimulatory effects on spermatogenesis. Baker et al., *Clin. Reprod. and Fert.*, 2: 161–174 (1983).

When sheep are immunized with inhibin or the inhibin α chain, their ovulation rate is increased, due to the immunoneutralization of endogenous inhibin. Cummins et al., *J. Reprod. Fertil.*, 77: 365 (1986); Henderson et al., *J. Endocrinol.*, 102: 305–309 (1984); Forage et al., *J. Endocrinol.*, 114: R1(1987); Al-Obaidi et al., *J. Reprod. Fert.*, 81: 403–414 (1987). The same effect has been observed in rats. Rivier and Vale, *Endocrinology*, 125: 152 (1989). In addition, Rivier and Vale suggest that increased FSH alone is sufficient to stimulate additional follicular growth and development, and the main mechanism through which treatment with anti-inhibin serum increases follicular development is through elevated plasma FSH levels. Other investigators reported that the administration of inhibin to sheep induces either anovulation or an increase in ovulation rate according to the scheme of treatment. Franchimont et al., *Rev. fr. Gynecol. Obstet.*, 83: 607 (1988).

The modulation of the inhibin subunit mRNAs during the rat estrus cycle has been intensely studied. Woodruff et al., *Science*, 239: 1296 (1988). Only recently has the integrative feedback relationship between ovarian inhibin and activin and pituitary FSH been partially elucidated. Hasegawa et al., in *Inhibin: Non-Steroidal Regulation of FSH Secretion*, ed. J. Burger et al., 42: 119–133 (New York: Raven Press, 1987); Woodruff et al., *Science*, 239: 1296–1299 (1988). Briefly, the ovary produces low levels of inhibin on the evening of proestrus. This allows FSH to remain elevated throughout the morning of estrus (secondary FSH surge). Rivier et al., *Science*, 234: 205–208 (1986). The secondary FSH surge recruits a new set of follicles into the ovulatory pool and is responsible for the initiation of inhibin subunit mRNA expression. As a consequence of inhibin production, pituitary FSH secretion is downregulated. Inhibin mRNA levels increase in maturing follicles as they progress through the cycle. Follicles that become atretic (non-ovulatory and highly steroidogenic) have little or no inhibin mRNA. Woodruff et al., in *Growth Factors and the Ovary*, ed. Hirshfield, pp. 291–295 (New York: Plenum Press, 1989). Inhibin subunit mRNA accumulation climaxes on the afternoon of proestrus in healthy follicles simultaneously with the primary LH and FSH surges. Woodruff et al., *Science*, supra.

Treatment of women with FSH or a mixture of FSH and LH to induce ovulation for in vitro fertilization results in increased inhibin serum levels during the follicular and early luteal phase of the cycle. McLachlan et al., *Lancet*, 1233–1234 (1986); Tsonis et al., *J. Clin. Endocrinol. Metab.*, 66: 915 (1988); Buckler et al., *J. Endocrin.*, 122: 279–285 (1989); Tsuchiya et al., *Fert. Steril.*, 52: 88 (1989). However, another investigator has found that at the time of ovulation neither inhibin activity nor follicular levels of steroid or gonadotropins are adequate criteria for predicting the eventual outcome of oocytes in an in vitro fertilization protocol. Lefevre et al., *Fert. Steril.*, 46: 325 (1986).

The polycystic ovarian disease is a heterogeneous clinical disorder manifested by oligo- or amenorrhea, infertility, hirsutism, obesity, and bilateral polycystic ovaries. Serum LH levels are often inappropriately elevated in relation to FSH levels. It has been speculated that in this disease, elevated serum inhibin levels may be involved in producing the discordant gonadotropin secretion by selectively inhibiting FSH release. Tanabe et al., *J. Clin. Endocrinol. Metab.*, 57: 24 (1983); Yen and Jaffe eds., *Reproductive Endocrinology*, ed 2 (Saunders, Philadelphia, 1986), p. 441. However, no evidence has been found of a primary defect in ovarian inhibin physiology in women with the disease in terms of either basal or gonadotropin-stimulated secretion. Buckler et al., *J. Clin. Endocrin. and Metabol.*, 66: 798 (1988).

Ovulation can be induced by the use of anti-estrogens, particularly clomiphene citrate, in some women with polycystic ovarian disease (Franks et al., *Clin. Obstet. Gynaecol.*, 12: 605 (1985)), but some of these women fail to respond. Garcia et al., *Fertil. Steril.*, 28: 707–717 (1977); Wan and Gemzell, *Fertil. Steril.*, 33: 479–486 (1980). Human menopausal gonadotropin is then used, but its use has been associated with high rates of abortion, multiple pregnancies, and hyperstimulation. Daily administration of progesterone combined with estrogen can result in normal pregnancies. A similar approach has been tried using the gonadotropin releasing hormone agonist buserelin. However, suppression of LH is difficult to achieve. Pure FSH is also being evaluated. Other methods of known treatment include surgery such as ovarian wedge resection and laparoscopic electrocautery.

It is an object of the present invention to provide a method for treating polycystic ovarian disease that is an effective treatment.

It is another object to provide a method for initiating follicular degeneration or inhibiting follicular maturation.

These and other objects will be apparent to those of ordinary skill in the art.

SUMMARY OF THE INVENTION

Accordingly, this invention provides a method for inhibiting the maturation of follicles in the ovary of a female mammal comprising administering to the ovary of the mammal an effective amount of activin.

In another aspect, this invention provides a pharmaceutical composition suitable for inhibiting the maturation of follicles in the ovary of a female mammal comprising an effective amount of activin in a pharmaceutically acceptable carrier.

In patients with polycystic ovarian disease, follicles are large and non-ovulatory. Activin treatment would halt follicular growth, resulting in normalization of ovulation. Furthermore, patients having premature ovarian failure resulting in early gonadal senescence could be treated with activin to slow the rate at which the follicles mature.

BRIEF DESCRIPTION OF THE DRAWINGS

FIG. 2 is a graph of the follicular distribution in inhibin- and activin-treated ovaries, with the asterisks indicating largely atretic responses.

DESCRIPTION OF THE PREFERRED EMBODIMENTS

Figure 1:
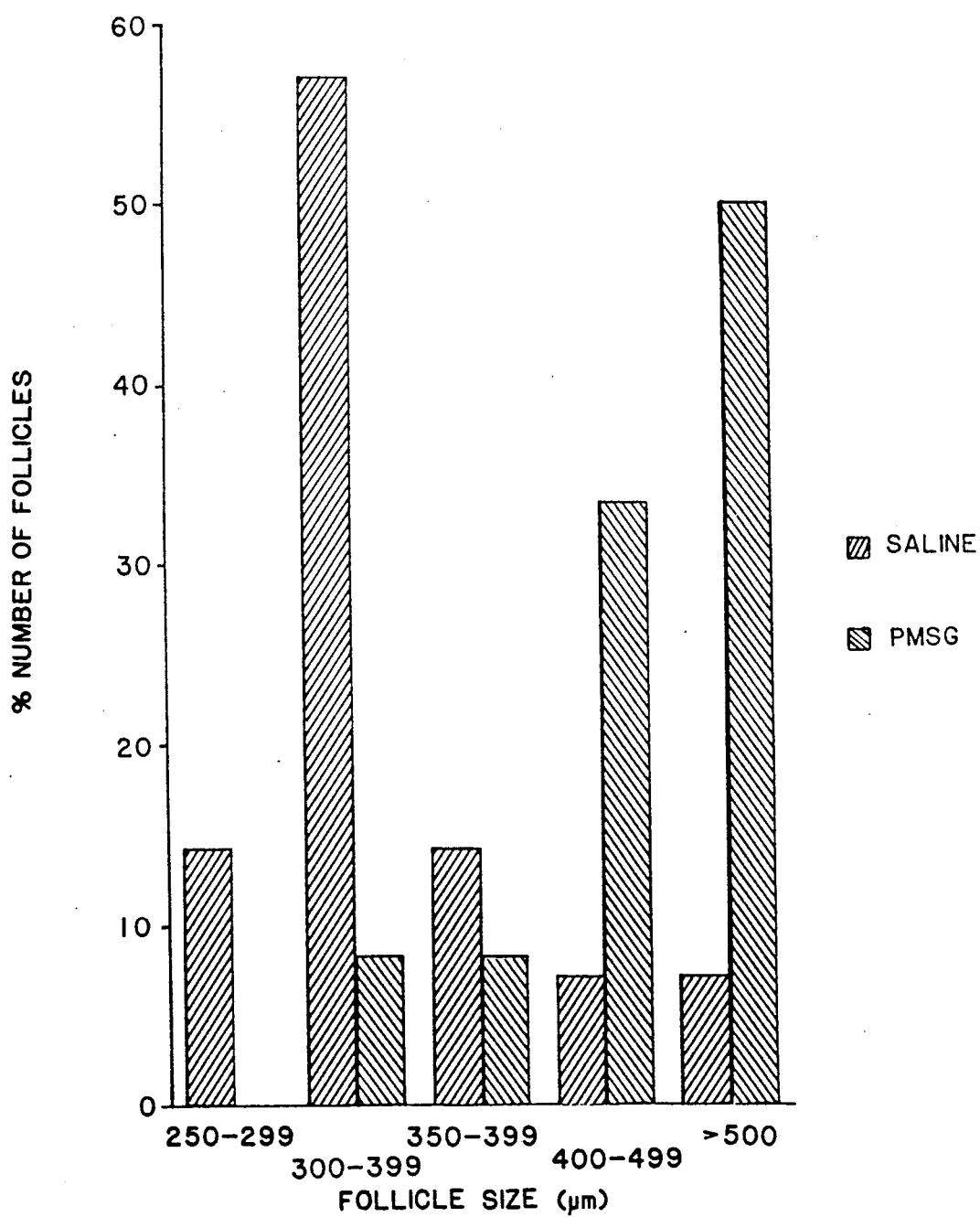
FIG. 1 is a graph of the follicular distribution in control (saline) and pregnant mare serum gonadotropin (PMSG)-treated ovaries of rats.

As used herein, the term "activin" refers to homo- or heterodimers of $\beta$ chains of inhibin, prepro forms, and pro forms, together with glycosylation and/or amino acid sequence variants thereof. After cleavage from the mature protein, the precursor portion may be non-covalently associated with the mature protein. Activin A refers to activin with the two chains of $\beta_A$. Activin AB refers to activin with the chains $\beta_A$ and $\beta_B$. Activin B refers to activin with the two chains of $\beta_B$.

The intact isolated prepro or prodomain or mature $\beta_A$ and $\beta_B$ sequences are suitably synthesized by any means, including synthetic and/or recombinant means, but are preferably synthesized in recombinant cell culture, for example, as described in U.S. Pat. No. 4,798,885 issued Jan. 17, 1989.

It is within the scope hereof to employ activin from animals other than humans, for example, porcine or bovine sources, to treat humans. For example, the nucleotide and deduced amino acid sequences of the porcine activin $\beta$ chain are found in FIGS. 2A and 2B of U.S Pat. No. 4,798,885, supra. Likewise, if it is desirable to treat other mammalian species such as domestic and farm animals and zoo, sports, or pet animals, human activin, as well as activin from other species, is suitably employed.

Generally, amino acid sequence variants will be substantially homologous with the relevant portion of the mammalian $\beta$ chain sequences set forth in, e.g., U.S. Pat. No. 4,798,885, supra. "Substantially homologous" means that greater than about 60% of the primary amino acid sequence of the homologous polypeptide corresponds to the sequence of the activin chain when aligned to maximize the number of amino acid residue matches between the two proteins. Alignment to maximize matches of residues includes shifting the amino and/or carboxyl terminus, introducing gaps as required, and/or deleting residues present as inserts in the candidate. Typically, amino acid sequence variants will be greater than about 70% homologous with the corresponding native sequences.

While the site for introducing a sequence variation is predetermined, it is unnecessary that the mutation per se be predetermined. For example, in order to optimize the performance of mutation at a given site, random mutagenesis may be conducted at the target codon or region and the expressed activin mutants screened for the optimal combination of desired activity. Techniques for making substitution mutations at predetermined sites in DNA having a known sequence are well known, for example, M13 primer mutagenesis.

Mutagenesis is conducted by making amino acid insertions, usually on the order of about from 1 to 10 amino acid residues, or deletions of about from 1 to 30 residues. Substitutions, deletions, insertions, or any subcombination may be combined to arrive at a final construct. Preferably, however, substitution mutagenesis is conducted. Obviously, the mutations in the encoding DNA must not place the sequence out of reading frame and preferably will not create complementary regions that could produce secondary mRNA structure.

Covalent modifications of activin are included within the scope of the invention, and include covalent or aggregative conjugates with other chemical moieties. Covalent derivatives are prepared by linkage of functionalities to groups that are found in the activin amino acid side chains or at the N- or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as aryl or alanyl; and N-acyl derivatives of the amino terminal amino acid or amino-group containing residues, e.g., lysine or arginine. The acyl group is selected from the group of alkyl moieties (including C3 to C10 normal alkyl), thereby forming alkanoyl species, and carbocyclic or heterocyclic compounds, thereby forming aroyl species. The reactive groups preferably are difunctional compounds known per se for use in crosslinking proteins to insoluble matrices through reactive side groups, e.g., m-maleimido-benzoyl-N-hydroxy succinimide ester. Preferred derivatization sites are at histidine residues.

The term "polycystic ovarian disease" represents a heterogeneous group of clinical disorders. Its main features are secondary amenorrhea or oligomenorrhea, anovulatory infertility, hirsutism, obesity, and bilateral polycystic ovaries. The characteristic biochemical abnormalities seen are an inappropriate elevation of serum LH in the presence of normal or low serum FSH levels and follicular phase levels of progesterone. Androgen levels are usually raised. Also high resolution ultrasound imaging can be used to accurately identify multiple cystic areas in the ovary. The criteria used to identify polycystic ovaries on pelvic ultrasonography are the presence of multiple small cystic areas (2–4 mm in diameter), an increase in ovarian stroma, and ovarian enlargement. Polycystic ovaries can be found occasionally in women with normal menstrual cycles, so the term polycystic ovarian disease should be restricted to those women with the clinical and ultrasound features.

The expression "administering to the ovary" means not only injection into the ovary as by intrabursal means, but also techniques that result in flooding the area surrounding the ovary with activin such that the activin is absorbed into the ovary. This may be accomplished by making an incision in the abdomen or through the ovary with or without the use of a laparoscope. In addition, the activin can be injected into a vessel that feeds the ovary, preferably using a microscopic procedure. Furthermore, the activin can be put into an implant that is placed near the ovary and through which the activin is absorbed into the ovary. Other techniques may be employed, provided that the result is that activin is applied locally to the ovary and is effective for the purposes stated herein.

The present invention concerns itself with using activin to inhibit the maturation of follicles in female mammals. This includes initiation of follicle regeneration as well as treating polycystic ovarian disease and premature ovarian senescence. Female mammals include, e.g., sports, zoo, pet, and farm animals such as dogs, cats, cattle, pigs, horses, monkeys, and sheep, as well as humans.

The activin is administered to the mammal by means of the ovary, as discussed above. The specific route of administration will depend, e.g., on the medical history of the patient.

The activin compositions to be used in the therapy will be formulated and dosed in a fashion consistent with good medical practice, taking into account the clinical condition of the individual patient, the method of administration, the scheduling of administration, and other factors known to practitioners. The "effective amount" for purposes herein is thus determined by such considerations.

As a general proposition, the total pharmaceutically effective amount of the activin administered per dose will be in the range of about 1 $\mu$g/kg/day to 10 mg/kg/day of patient body weight, although, as noted above, this will be subject to a great deal of therapeutic discretion. Preferably, this dose is no more than about 10 $\mu$g/kg/day. The key factor in selecting an appropriate dose is the result obtained, as measured by increases in atresia or decreases in follicular development or by other criteria as deemed appropriate by the practitioner.

For administration, the activin is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the activin uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, nitrate, and other organic acid salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium, and/or nonionic surfactants such as Tween, Pluronics, or PEG.

The activin is typically formulated in such vehicles at a concentration of about 0.1 mg/ml to 100 mg/ml at physiological pH. It will be understood that use of certain of the foregoing excipients, carriers, or stabilizers will result in the formation of activin salts.

Activin to be used for therapeutic administration must be sterile. Sterility is readily accomplished by filtration through sterile filtration membranes (e.g., 0.2 micron membranes).

Therapeutic activin compositions generally are placed into a container having a sterile access port, for example, a vial having a stopper pierceable by a hypodermic injection needle.

Activin ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous activin solution, and the resulting mixture is lyophilized. The infusion solution is prepared by reconstituting the lyophilized activin using 5 ml of sterile water or Ringer's solution.

The invention will be more fully understood by reference to the following examples. They should not, however, be construed as limiting the scope of the invention. All literature and patent citations are expressly incorporated by reference.

EXAMPLE I

Twenty-five-day-old female Sprague-Dawley rats (Charles River Laboratories, Inc., Wilmington, Mass.) were anesthetized with a combination of 80 mg/kg of ketamine HCl (Vetlalar, Aveco Company) and 4 mg/kg xylozine (Gemini, Rugby Laboratories). The left dorsal lumbar region of the rat was then clipped and prepared with 70% isopropyl alcohol and an iodine scrub solution. A 5–7 mm incision was made through the dermal layers, just caudal to the last rib, followed by a 3–5-mm cut into the peritoneum. The ovary was then visualized and gently exteriorized by grasping the surrounding fat. Placing a pair of straight-eye dressing forceps between the left horn of the uterus and the surrounding fat and allowing them to open presented the ovary for injection. While the attached fat was grasped for stabilization, 10 $\mu$l of human recombinant activin A or inhibin A (prepared and purified as described in U.S. Pat. No. 4,798,885 issued Jan. 17, 1989, where inhibin A refers to inhibin with the chains $\alpha$ and $\beta_A$) was injected (1 $\mu$g/ovary) intrabursally caudal to the oviduct through a 28-gauge needle attached to a tuberculin syringe. PMSG, which is a combination of FSH and LH, was injected intraperitoneally at 25 international units (IU).

Animals were divided into the following groups:
Group 1: saline (n=5);
Group 2: PMSG (n=6);

Group 3: activin A (n=7);
Group 4: activin A and PMSG (n=8);
Group 5: inhibin A (n=8);
Group 6: inhibin A and PMSG (n=7).

The total number of animals used in each experiment is given in parenthesis; this represents two independent repetitions. 3H-Thymidine (1 µCi) was coinjected intrabursally with the hormones indicated below in an additional set of animals:

Group 7: 3H-thymidine in saline;
Group 8: 3H-thymidine and PMSG;
Group 9: 3H-thymidine and activin A;
Group 10: 3H-thymidine, activin A, and PMSG.

For each animal one ovary was injected with hormone and the other ovary served as the contralateral control. Dose volume was approximately 10 µl. Immediately post-dosing, slight pressure was applied to the injection site with a cotton applicator stick. The ovary was then carefully replaced, the incision was closed with two 9-mm wound clips, and the animal was returned to its cage and observed until it had recovered its righting reflex.

Necropsy was performed twenty-four hours after dosing. Tissue samples were collected and placed in 4% formalin in preparation for histological analysis.

Ovaries were allowed to fix 12 hours in 4% formalin, embedded in paraffin, and sectioned at 3 µm. Step sections were mounted onto microscope slides every 50-µm. 50 µm intervals were chosen based on oocyte diameter (80 µM) such that each follicle would be analyzed without redundancy. Sections were stained with hemotoxylin-eosin. Healthy vs. atretic follicles were scored morphologically by the following criteria: oocyte appearance, alignment of granulosa cell layer, and number of granulosa cell layer. Woodruff et al., in *Growth Factors and the Ovary*, ed., A. N. Hirshfield, pp. 291–295 (New York: Plenum Press, 1989); Osman, *J. Reprod. Fertil.*, 73: 261–270 (1985).

Ovaries treated with 3H-thymidine were fixed analogously to non-radioactive samples and sectioned at 3 µM. Slides were dipped in autoradiographic emulsion, exposed for 2–4 weeks at 4° C., and stained.

Follicular diameter was determined using the Bioquant TM image analysis system. Two measurements were taken at right angles to each other at the level of the granulosa cell bridge to the cumulus and oocyte. Duplication of measurements was avoided by holding the first section image in memory and then juxtaposing it to the subsequent section. Follicles that had been measured in the first section were not used.

FIG. 1 shows the number of follicles in each size class following intrabursal injection of saline or PMSG for a representative set of animals. FIG. 2 shows the number of follicles in each size class following intrabursal injection of inhibin A or activin A for a representative set of animals.

Saline-injected and untreated (contralateral) ovaries were similar in distribution of follicles. Animals treated with PMSG had follicles distributed from small (250 µm) to large (>500 µm). Inhibin treatment also caused a wave of follicles moving into larger-size classes, although this change was not as pronounced as in PMSG-treated animals. The effect of inhibin on follicular size of PMSG-treated animals was no different from PMSG treatment alone.

Treatment with activin resulted in atretic follicles, as indicated by the asterisks. Interestingly, activin treatment in a PMSG background resulted in a follicular distribution similar to PMSG alone. Follicular size is an indicator of fertility; the size of the follicle increases as it matures and prepares to ovulate and thus is a morphological marker of the maturing oocyte.

Follicular health was also monitored by following incorporation of 3H-thymidine into growing follicles. Saline-treated prepubertal follicles showed low levels of incorporation in mural granulosa cells, theca cells, and cells of the discus proligerus (cells of the cumulus and adjoining cells). Not all follicles in this treatment group were labeled. PMSG treatment resulted in a stimulation of follicular growth with concomitant enhancement of 3H-thymidine incorporation into dividing granulosa and theca cells. Moreover, most follicles of several size classes incorporated label.

Morphologically, activin-treated follicles are atretic. This is further supported by the lack of 3H-thymidine incorporation into granulosa or theca cells. Activin and PMSG therapy resulted in follicles that displayed no morphological signs of atresia but whose thymidine incorporation was reduced similar to those in saline-injected controls.

In conclusion, the in vivo studies here demonstrate unexpectedly that activin is an intragonadal down-regulator of reproductive function. Thus, patients with premature ovarian failure resulting in early gonadal senescence are suitably treated with activin to slow the rate of follicular maturation. Further, patients with polycystic ovarian disease should also benefit from activin therapy.

What is claimed is:

1. A method for inhibiting the maturation of follicles in the ovary of a female mammal comprising administering to the ovary of the mammal an effective amount of activin.

2. The method of claim 1 wherein the activin is porcine or human activin A, activin AB, or activin B.

3. The method of claim 2 wherein the activin is human activin A.

4. The method of claim wherein the administration is by injection into the ovary.

5. The method of claim 1 wherein the mammal is human.

6. The method of claim 1 wherein the effective amount is a daily dose of about 1 µg/kg to 10 mg/kg.

7. The method of claim 1 wherein the female mammal has polycystic ovarian disease or premature ovarian senescence.

* * * * *